United States Patent
Feyh et al.

(10) Patent No.: US 9,863,901 B2
(45) Date of Patent: Jan. 9, 2018

(54) SEMICONDUCTOR SENSOR HAVING A SUSPENDED STRUCTURE AND METHOD OF FORMING A SEMICONDUCTOR SENSOR HAVING A SUSPENDED STRUCTURE

(71) Applicant: Robert Bosch GmbH, Stuttgart (DE)

(72) Inventors: Ando Feyh, Reutlingen (DE); Gary O'Brien, Palo Alto, CA (US); Ashwin K. Samarao, Mountain View, CA (US); Fabian Purkl, Gerlingen (DE); Gary Yama, Mountain View, CA (US)

(73) Assignee: Robert Bosch GmbH, Stuttgart (DE)

( * ) Notice: Subject to any disclaimer, the term of this patent is extended or adjusted under 35 U.S.C. 154(b) by 350 days.

(21) Appl. No.: 14/549,400

(22) Filed: Nov. 20, 2014

(65) Prior Publication Data
US 2015/0160145 A1    Jun. 11, 2015

Related U.S. Application Data

(60) Provisional application No. 61/913,064, filed on Dec. 6, 2013.

(51) Int. Cl.
| | |
|---|---|
| *G01N 27/12* | (2006.01) |
| *G01N 27/02* | (2006.01) |
| *G01N 33/00* | (2006.01) |

(52) U.S. Cl.
CPC .......... *G01N 27/028* (2013.01); *G01N 27/12* (2013.01); *G01N 33/0062* (2013.01)

(58) Field of Classification Search
CPC .............................. G01N 27/028; G01N 27/12
(Continued)

(56) References Cited

U.S. PATENT DOCUMENTS

| | | |
|---|---|---|
| 4,984,446 A | 1/1991 | Yagawara et al. |
| 5,786,608 A | 7/1998 | Lescouzeres et al. |
| (Continued) | | |

FOREIGN PATENT DOCUMENTS

EP    0751389 A1    1/1997

OTHER PUBLICATIONS

International Search Report and Written Opinion corresponding to PCT Application No. PCT/EP2014/076249, dated Feb. 17, 2015 (12 pages).
(Continued)

*Primary Examiner* — Walter L Lindsay, Jr.
*Assistant Examiner* — Philip Marcus T Fadul
(74) *Attorney, Agent, or Firm* — Maginot Moore & Beck LLP

(57) ABSTRACT

A semiconductor gas sensor device includes a substrate, a conductive layer supported by the substrate, a non-suitable seed layer, and a porous gas sensing layer portion. The non-suitable seed layer is formed from a first material and includes a first support portion supported by the conductive layer, a second support portion supported by the conductive layer, and a suspended seed portion extending from the first support portion to the second support portion and suspended above the conductive layer. The porous gas sensing layer portion is formed from a second material and is supported directly by the non-suitable seed layer in electrical communication with the conductive layer. The first material and the second material form a non-suitable pair of materials.

13 Claims, 11 Drawing Sheets

(58) Field of Classification Search
USPC .......................................................... 73/31.06
See application file for complete search history.

(56) References Cited

U.S. PATENT DOCUMENTS

2004/0163444 A1    8/2004  Dimeo, Jr. et al.
2010/0212403 A1*  8/2010  Seal ..................... G01N 33/005
                                                                     73/31.06
2011/0207328 A1*  8/2011  Speakman .......... H01L 51/0016
                                                                     438/694

OTHER PUBLICATIONS

Grudin, O. et al., "High-Temperature Gas Sensor Using Perovskite Thin Films on a Suspended Microheater", Journal of Vacuum Science and Technology, vol. 20, No. 3, May 1, 2002, pp. 1100-1104 (5 pages).

Kook-Nyung, Lee et al., "A High-Temperature MEMS Heater Using Suspended Silicon Structures", Journal of Micromechanics & Microengineering, vol. 19, No. 11, Nov. 1, 2009, pp. 1-8 (8 pages).

* cited by examiner

SEMICONDUCTOR SENSOR HAVING A SUSPENDED STRUCTURE AND METHOD OF FORMING A SEMICONDUCTOR SENSOR HAVING A SUSPENDED STRUCTURE This application claims the benefit of priority of U.S. provisional application Ser. No. 61/913,064, filed on Dec. 6, 2013, the disclosure of which is herein incorporated by reference in its entirety.

FIELD

This disclosure relates generally to sensor devices and particularly to a thin-film gas sensor device having a suspended structure.

BACKGROUND

One type of semiconductor sensor is a gas sensor device. Semiconductor gas sensors are used to detect the presence of a particular gas or gasses in an environment to which the sensor is exposed. A common type of gas sensor is a metal oxide semiconductor (MOS) gas sensor. MOS gas sensors, which are also referred to as "thick-film" gas sensors, typically include a heating element and a gas-sensitive portion located between two electrodes. The heating element is activated to heat the gas-sensitive portion to a temperature that is suitable for detecting a target gas. The gas-sensitive portion is a thick-film that is configured to undergo an electrical change in the presence of the target gas. The electrical change of the gas-sensitive portion is detected by an external circuit that is electrically connected to the gas sensor.

FIGS. 24 and 25 show part of a gas-sensitive portion 10 of a prior art MOS gas sensor. The gas-sensitive portion 10 is typically formed from a polycrystalline material that includes numerous grains 20. The region of contact between the grains 20 is referred to herein as a grain boundary 22. The grain boundaries 22 are target sites to which molecules of the target gas bind through a process referred to as adsorption. When adsorption of the target gas occurs, the gas-sensitive portion 10 undergoes the above-described electrical change that is detected by the external circuit.

Chemisorption is one type of adsorption that may occur at the grain boundaries 22 in the presence of the target gas. To illustrate the effects of chemisorption, FIG. 24 includes a graph showing an electrical potential barrier at the grain boundary 22 in the presence of air containing oxygen molecules. For an electron 30 to move through the grain boundary 22, it requires enough energy to overcome the potential barrier, which defines a reference magnitude measured in electronvolts (eV). A combination of the potential barriers of all/most of the grain boundaries 22 in the gas-sensitive portion 10 contributes to an electrical resistance of the gas-sensitive portion.

In FIG. 25, the exemplary grain boundary 22 is shown in the presence of molecules of a reducing gas. Chemisorption of the reducing gas has caused a reduction in the magnitude of the potential barrier due to donor electrons from the reducing gas. When the potential barriers are combined, the overall electrical resistance of the gas-sensitive portion 10 is reduced due to the reduction in the magnitude of at least some of the potential barriers at the grain boundaries 22 at which reduction has occurred. The exemplary reduction in electrical resistance of the gas-sensitive portion 10 is detectable by the external circuit connected to the gas sensor as being indicative of the presence of a target gas. Although not shown, in the presence of an oxidizing gas, the magnitude of the potential barrier increases, thereby resulting in an increase in the electrical resistance of the gas-sensitive portion 10, which is also detectable by the external circuit connected to the gas sensor as being indicative of the presence of a target gas.

Heterogeneous catalysis is another process that may occur at the grain boundaries 22, depending on the type gas near the gas-sensitive portion 10. One example of heterogeneous catalysis, referred to as carbon monoxide (CO) oxidation, results in the oxidation of a carbon dioxide ($CO_2$) molecule, due to the presence of a carbon monoxide molecule and an oxygen molecule located near one of the grain boundaries 22 of the gas-sensitive portion 10. Heterogeneous catalysis, in at least some instances, results in an electrical change of the gas-sensitive portion 10, which is detectable by the external circuit connected to the gas sensor as being indicative of the presence of a target gas.

In addition to preparing the gas-sensitive portion for detecting and/or exposure to the target gas through adsorption, the heating element is also activated to "reset" the gas sensor through a process referred to as desorption. During desorption molecules are evacuated from the gas-sensitive portion in order to prepare the sensor for sensing additional quantities of the target gas or for sensing a different type/species of target gas.

When the heating element of the typical MOS gas sensor is activated, other portions of the gas sensor are heated in addition to the gas-sensitive portion. For example, if an intermediary layer is located between the heating element and the gas-sensitive portion, then the heating element heats the intermediary layer in addition to heating the gas-sensitive portion. Furthermore, if the heating element is positioned in contact with or in proximity to a base layer, a substrate layer, or a handle layer, then heat energy from the heating element may undesirably/unnecessarily be transferred thereto. Additionally, since the gas-sensitive portion of a MOS gas sensor is a "thick-film," heating of the gas-sensitive portion has an associated time-constant that may be of longer duration than desired. Accordingly, in the typical MOS gas sensor, energy consumed by the heating element is used to heat portions of the gas sensor that are not desired to be heated, and heating the gas-sensitive portion may consume more time than desired.

Therefore, for at least some of the above-described reasons, it is desirable to structure the gas sensor so that the heat energy generated by the heating element heats the gas-sensitive portion of the gas sensor quickly and without significantly heating other parts of the gas sensor. Accordingly, further developments in the area of gas sensors are desirable.

SUMMARY

According to an exemplary embodiment of the disclosure, a semiconductor gas sensor device includes a substrate, a conductive layer supported by the substrate, a non-suitable seed layer, and a porous gas sensing layer portion. The non-suitable seed layer is formed from a first material and includes a first support portion supported by the conductive layer, a second support portion supported by the conductive layer, and a suspended seed portion extending from the first support portion to the second support portion and suspended above the conductive layer. The porous gas sensing layer portion is formed from a second material and is supported directly by the non-suitable seed layer in electrical communication with the conductive layer. The first material and the second material form a non-suitable pair of materials.

According to another exemplary embodiment of the disclosure, a method of fabricating a semiconductor sensor device includes forming a conductive layer above a substrate, and patterning the conductive layer to define a first isolated portion of the conductive layer that is electrically isolated from a second isolated portion of the conductive layer, and forming a sacrificial layer above the conductive layer. The method further includes patterning the sacrificial layer to define a first trench portion exposing an upper surface of the first isolated portion, a second trench portion exposing an upper surface of the second isolated portion, and a suspended trench portion that does not expose the conductive layer and that extends from the first trench portion to the second trench portion. Additionally, the method includes forming a non-suitable seed layer from a first material in the first trench portion, the second trench portion, and the suspended trench portion, and forming a porous gas sensing layer portion from a second material on the non-suitable seed layer and in electrical communication with the conductive layer. The first material and the second material form a non-suitable pair of materials. The method also includes removing the sacrificial layer to suspend a suspended portion of the seed layer and the porous gas sensing layer portion above the conductive layer.

According to yet another exemplary embodiment of the disclosure, a method of operating a semiconductor gas sensor device includes applying an electrical current directly to a porous gas sensing layer portion formed from a first material. The porous gas sensing layer portion is suspended above a conductive layer and is supported directly by a non-suitable seed layer portion that is formed from a second material and is suspended above the conductive layer. The first material and the second material form a non-suitable pair of materials. The method further includes heating the porous gas sensing layer portion to a predetermined temperature, exposing the heated porous gas sensing layer portion to at least one gas, and sensing an electrical property of the porous gas sensing layer portion after exposing the heated porous gas sensing layer portion to the at least one gas.

BRIEF DESCRIPTION OF THE FIGURES

The above-described features and advantages, as well as others, should become more readily apparent to those of ordinary skill in the art by reference to the following detailed description and the accompanying figures in which.

DETAILED DESCRIPTION

Figure 1:
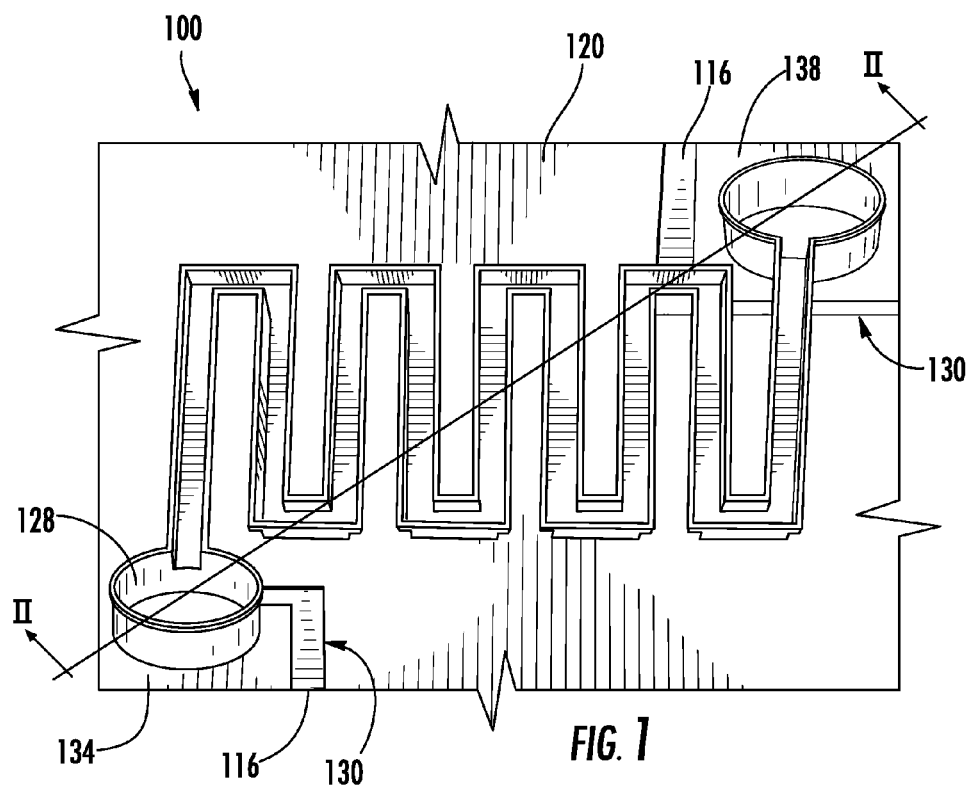
FIG. 1 is perspective view of a gas sensor device, as described herein, the sensor device includes a thin-film heater and gas-sensitive portion that is suspended above a substrate of the sensor device so that the heat energy generated by the heater heats the gas-sensitive portion quickly and without significantly heating other parts of the sensor device.

For the purpose of promoting an understanding of the principles of the disclosure, reference will now be made to the embodiments illustrated in the drawings and described in the following written specification. It is understood that no limitation to the scope of the disclosure is thereby intended. It is further understood that this disclosure includes any alterations and modifications to the illustrated embodiments and includes further applications of the principles of the disclosure as would normally occur to one skilled in the art to which this disclosure pertains.

Figure 2A:
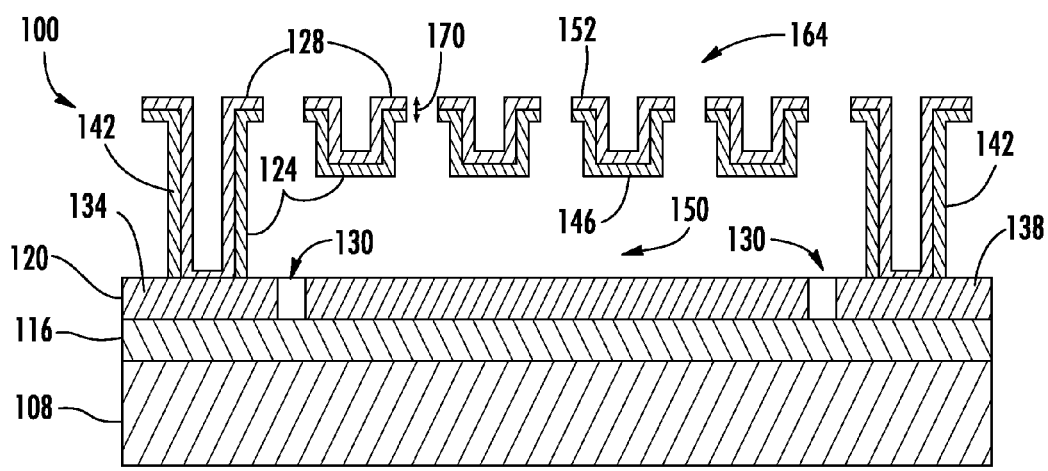
FIG. 2A is a cross sectional view taken along line II-II of FIG. 1, showing the thin-film heater and gas-sensitive portion suspended above the substrate, a seed layer is also shown suspended above the substrate.

A semiconductor sensor assembly, which in this embodiment is a gas sensor device 100, is shown in FIGS. 1 and 2A. The exemplary embodiment of the sensor device 100 includes a substrate 108 (FIG. 2A), an insulator layer 116, an electrically conductive layer 120, a seed layer 124 (FIG. 2A), and a gas-sensitive layer 128. The substrate 108 is formed from silicon or another desired type of substrate.

The insulator layer 116, in one embodiment, is a deposited dielectric such as, silicon dioxide ($SiO_2$). The insulator layer 116 is deposited over the substrate 108. In another embodiment, the insulator layer 116 is formed from any suitable electrically insulating material.

The electrically conductive layer 120 is formed over the insulator layer 116. In one embodiment, the conductive layer 120 is formed from platinum (Pt). Openings 130 in the conductive layer 120 electrically isolate a left isolated portion 134 from a right isolated portion 138 of the conductive layer.

The seed layer 124 is a thin-film that defines two support portions 142 and a suspended serpentine portion 146 (also referred to herein as a suspended seed portion). The support portions 142 are formed over and are supported by the conductive layer 120 and extend upward from the isolated portions 134, 138. The serpentine portion 146 extends from one support portion 142 to the other support portion 142 and is suspended above the conductive layer 120. The serpentine portion 146 is spaced apart from the conductive layer 120, such that there is a space 150 between the serpentine portion and the conductive layer. The serpentine portion 146 defines a substantially U-shaped trench in cross section that provides mechanical stability to the serpentine portion. The seed layer 124, in one embodiment, is formed from aluminum oxide ($Al_2O_3$). In another embodiment, the seed layer 124 is formed from another suitable material that provides mechanical stability.

The gas-sensitive layer 128 (also referred to herein as a porous gas sensing layer portion) is a thin-film that is formed on the seed layer 124 and is supported directly by the seed layer. The gas-sensitive layer 128 defines a suspended sensing portion 152 that is supported directly by the suspended seed portion 146. In one embodiment, the gas-sensitive layer 128 is formed from platinum. The gas-sensitive layer 128 is in electrical communication with the conductive layer 120. Specifically, the gas-sensitive layer 128 is electrically connected to the left portion 134 and the right portion 138 of the conductive layer 120. The shape of the gas-sensitive layer 128 corresponds to the shape of the seed layer 124; accordingly, in one embodiment, at least a portion of the gas-sensitive layer defines a substantially U-shaped trench in cross section. Besides being sensitive to a target gas, the gas-sensitive layer 128 may also be configured as heater.

Figure 2B:
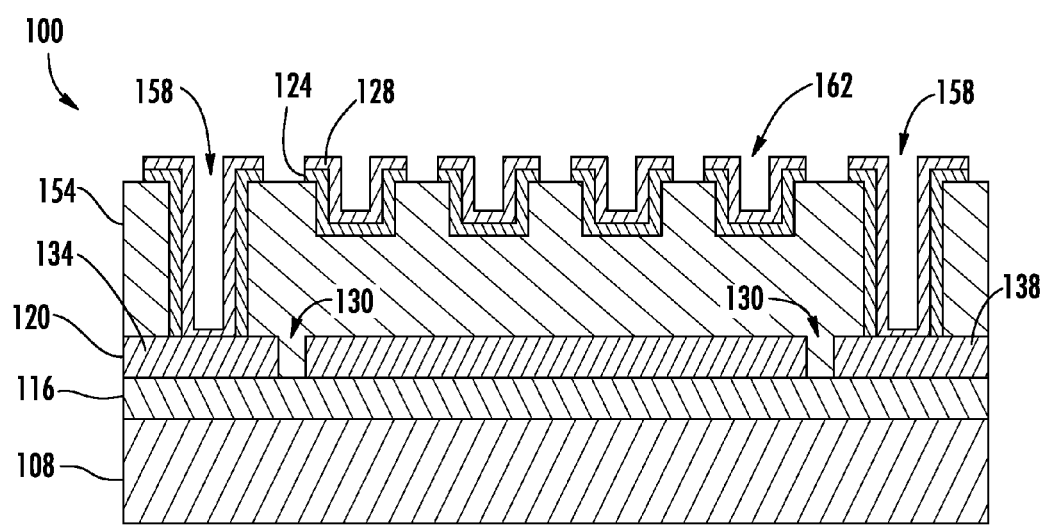
FIG. 2B is a cross sectional view taken along a line similar to the line II-II of FIG. 1, showing a sacrificial poly-silicon layer included with the sensor device.

With reference to FIG. 2B, the sensor device 100 is fabricated/manufactured according to the following process. First, the substrate 108 is provided. Second, the insulator layer 116 is formed over the substrate 108. In the illustrated embodiment, the insulator layer 116 is formed using any desired chemical or physical deposition process.

Next, the conductive layer 120 is formed on the insulator layer 116 above the substrate 108. In one embodiment, atomic layer deposition (ALD) is used to form the conductive layer 120; however, any suitable chemical or physical deposition process may be used. Then, the conductive layer 120 is patterned by trenching, for example, to define the openings 130 and the isolated portions 134, 138.

Thereafter, a sacrificial layer 154 is deposited on the conductive layer 120. Then, the sacrificial layer 154 is patterned by trenching, for example, two post trenches 158 and a suspended serpentine trench 162 that extends from a first post trench (left, for example) to a second post trench (right, for example). The post trenches 158 expose an upper surface of the isolated portions 134, 138; whereas, the suspended serpentine trench 162 does not expose any portion of the conductive layer 120. In one embodiment, the sacrificial layer 154 is formed from poly-silicon; however, the sacrificial layer may be formed from any suitable material.

Next, the seed layer 124 is deposited onto the sacrificial layer 154 using ALD. In particular, material of the seed layer 124 is deposited into the post trenches 158 and the suspended serpentine trench 162. Since ALD is used, the seed layer 124 is formed as a thin-film that conforms to the surfaces of the post trenches 158 and the serpentine trench 162.

Then, the gas-sensitive layer 128 is deposited on the seed layer 124 using ALD. Since ALD is used, the gas-sensitive layer 128 is formed as a thin-film that conforms to the surfaces of the seed layer 124. The gas-sensitive layer 128 is deposited to be in electrical communication with the conductive layer 120. Specifically, a first end (left side in FIG. 2B) of the layer 128 is in electrical communication with the isolated portion 134 and a second end (right side in FIG. 2B) is in electrical communication with the isolated portion 138.

After forming the gas sensitive layer 128 and the seed layer 124, the layers 124, 128 may be patterned to finalize their shape. Then, the sacrificial layer 154 is released/ removed using xenon difluoride (XeF$_2$) or any other suitable release agent. Removal of the sacrificial layer 154 suspends the serpentine portion 146 and the suspended sensing portion 152 above the conducting layer 120.

The illustrated embodiment of the sensor device 100 includes a two layer suspended portion 164 (FIG. 2A) that includes the serpentine portion 146 of the seed layer 124 and the suspended sensing portion 152 of the gas-sensitive layer 128. In other embodiments, however, any number of thin-film layers may be included in the suspended portion 164. For example, the suspended portion 164 may include only one layer and, thus, would be composed of the gas-sensitive layer 128 only (which also functions as a heater). In another embodiment, multiple instances of the gas-sensitive layer 128 are separated by one or more seed layers 124. A specific example would be a suspended portion 164 that includes two seed layers interlaced with three gas-sensitive layers to form a suspended portion 164 including five thin-film layers.

Even though the sensor device 100 is described as a thin-film sensor device, the sensor device 100 could also be formed using a MOS structure including thick-film layers.

In operation, the sensor device 100 is configured to sense the presence of a target gas or target gasses in a space in which the sensor device is positioned. Exemplary target gasses include carbon monoxide, nitrogen dioxide (NO$_2$), ammonia (NH$_3$), methane (CH$_4$), volatile organic compounds (VOCs), and the like. Due at least to the small size of the sensor device 100, as compared to prior art MOS gas sensors, the sensor device 100 is usable to detect gasses in a variety of applications such as automobile exhaust systems, home appliances, laptops, handheld or portable computers, mobile telephones, smart phones, wireless devices, tablets, personal data assistants (PDAs), portable music players, film cameras, digital cameras, GPS receivers and other satellite navigation systems, electronic reading displays, projectors, cockpit controls, game consoles, earpieces, headsets, hearing aids, wearable display devices, security systems, and other applications as desired by those ordinary skill in the art.

Use of the sensor device 100 includes applying an electrical current directly to the gas-sensitive layer 128 with an electrical energy source (not shown). In response to the electrical current, the gas-sensitive layer 128 is quickly heated to a desired sensing temperature (i.e. a predetermined temperature) that is based at least on a magnitude of the electrical energy source and an electrical resistance of the suspended portion 164. A very low heating power is used to heat the gas-sensitive layer 128 to the desired sensing temperature due to the layer 128 being suspended and due to the layer 128 being very thin (i.e. thickness 170, FIG. 2A). Also, the suspended structure enables the gas-sensitive layer 128 to be heated to a first temperature while enabling the substrate 108, the insulator layer 116, and the conductive layer 120 to remain at a second temperature that is different (i.e. lower) than the first temperature. Since the gas-sensitive layer 128 is spaced apart from the insulator layer 116 and the substrate 108, substantially no heat energy is used to heat the insulator layer and the substrate during heating of the gas-sensitive layer 128. Although some of the heat energy developed by the layer 128 is used to heat the air surrounding the layer 128 (including air in the space 150), substantially all of the heat energy is used to heat the layer 128. Furthermore, the serpentine shape of the suspended portion 164 results in the gas-sensitive layer 128 efficiently converting electrical energy into heat energy.

The sensing temperature of the gas-sensitive layer 128 is based on properties of the target gas and the environment/space in which the assembly 100 is positioned. Exemplary sensing temperatures range from one hundred fifty degrees Celsius to five hundred degrees Celsius; however, the sensor device 100 is configurable to operate at any desired sensing temperature.

The gas-sensitive layer 128 is heated to the sensing temperature within a heating time period, which is referred to herein as a thermal time constant and a predetermined time period. The thermal time constant begins when electrical energy is applied to the layer 128 and ends when the layer 128 is heated to the sensing temperature. Due at least to the thinness and the structure of the gas-sensitive layer 128, the sensor device 100 has an extremely low thermal time constant on the order of 0.1 milliseconds to ten milliseconds. Furthermore, the gas-sensitive layer 128 is configured for fast temperature changes, ultimately resulting in fast detection of the target gas.

After being heated, the sensor device 100 is exposed to a space in which at least one gas is present. A target gas may or may not be included in the at least one gas. Thereafter, an electrical property of the gas-sensitive layer 128 is sensed by an external circuit (not shown). In one embodiment, a voltage drop across a resistor (not shown) connected in series with the gas-sensitive layer 128 is detected/monitored by the external circuit to determine the presence, absence, and/or concentration of the target gas. Typically, if the target gas is present and is an oxidizing gas, then as the target gas binds to the gas-sensitive layer 128 via adsorption and/or chemisorption, the electrical resistance of the layer 128 is increased and a decrease in magnitude of the voltage dropped across the resistor is detected by the external circuit. If the target gas is present and is a reducing gas, then as the target gas binds to the gas-sensitive layer 128 via adsorption and/or chemisorption, the electrical resistance of the layer 128 is decreased and an increase in magnitude of voltage dropped across the resistor is detected by the external circuit.

In other embodiments, the sensor device 100 is operable to sense the target gas using any other desired transduction principle including, but not limited to, resistive, capacitive, and resonant frequency.

In addition to preparing the gas-sensitive layer 128 for detecting and/or exposure to the target gas, the layer 128 may also be heated to "reset" the gas sensor 100 through desorption. During desorption molecules are evacuated from the gas-sensitive layer 128 in order to prepare the sensor 100 for sensing additional quantities of the target gas or for sensing a different type/species of target gas.

Figure 3:
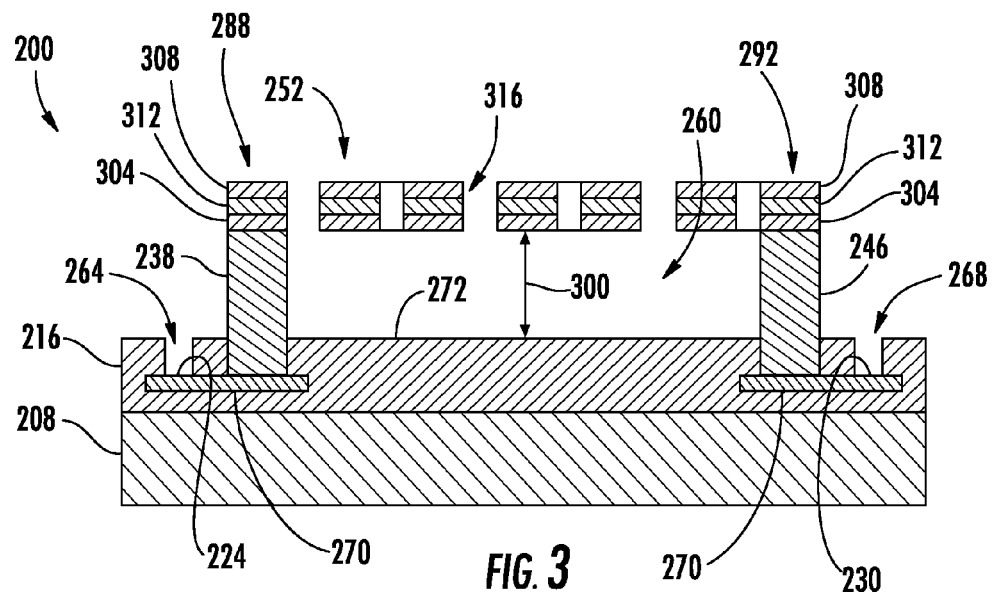
FIG. 3 is a cross sectional view of another embodiment of a thin-film gas sensor device, as described herein, taken along line III-III of FIG. 4, the sensor device includes a heater and two gas-sensitive portions that are suspended above a substrate of the sensor device so that the heat energy generated by the heater heats the gas-sensitive portions without significantly heating other parts of the sensor device.
Figure 4:
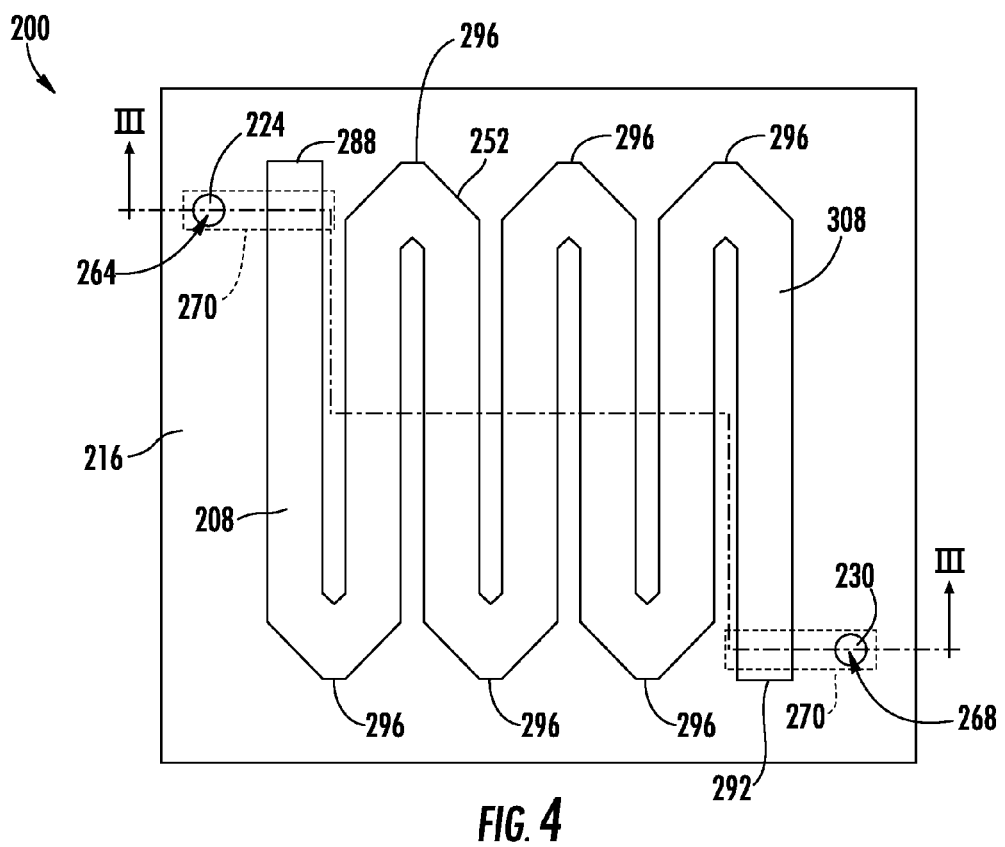
FIG. 4 is a top plan view of the sensor device of FIG. 3, showing a serpentine shape of the suspended portions.

Another embodiment of a gas sensor device 200 is shown in FIGS. 3 and 4. The exemplary embodiment of the sensor device 200 includes a substrate 208, an insulator layer 216, bond pads 224, 230, support structures 238, 246, and a suspended portion 252 that is suspended above and spaced apart from the insulator layer 216, such that an air space 260 is located between the suspended portion and the insulator layer. The substrate 208 in one embodiment is formed from silicon or another desired type of substrate.

The insulator layer 216, in one embodiment, is a deposited dielectric such as, silicon dioxide (SiO$_2$). The insulator layer 216 defines access openings 264, 268 configured to provide access to the bond pads 224, 230 respectively, within the insulator layer 216.

The bond pads 224, 230 (also referred to herein as bonding pads) are conductively connected to respective buried feed-throughs 270, which extend within the insulator layer 216 to the support structures 238, 246. The bond pads 224, 230 and the feed-throughs 270 are formed from metal or another conductive material and are configured to be electrically connected to an external circuit(s) (not shown) configured to operate the sensor device 200.

With continued reference to FIGS. 3 and 4, the support structures 238, 246, which are also referred to herein as support posts or supports, extend upwardly from the buried feed-throughs 270 and are configured to support the suspended portion 252 at a location above an upper surface 272 (FIG. 3) of the insulator layer 216. The support structures 238, 246 of the illustrated embodiment are substantially square or rectangular as viewed from the top (see FIG. 13), and are electrically connected to the bond pads 224, 230 and the feed-throughs 270.

The suspended portion 252 (also referred to herein as a suspended structure) is a thin-film stack configured to define a first end 288 that is electrically connected to the support structure 238 and a second end 292 that is electrically connected to the other support structure 246. The suspended portion 252 is free-standing and is thermally isolated from the insulator layer 216. The suspended portion 252 defines a serpentine shape that includes six bends 296 (FIG. 4) (other embodiments have a different number of bends). In the illustrated embodiment, the direction of extension of the suspended portion 252 changes by approximately one hundred eighty degrees at each of the bends 296. The suspended portion 252 is suspended at a height 300 (FIG. 3) above the upper surface 272 of the insulator layer 216, and the air space 260 is a void defined between the insulator layer and the suspended portion.

As shown in FIG. 3, the suspended portion 252, in one embodiment, includes a lower (first) thin-film gas-sensitive portion 304, an upper (second) thin-film gas-sensitive portion 308, and a thin-film heater 312 located therebetween. The gas-sensitive portions 304, 308 (also referred to herein as sensing layers and/or catalytic metal sensing layers) are electrically connected to the heater 312 and the support structures 238, 246. Accordingly, suspended portion 252 is configured to enable electrical current to flow between the support structures 238, 246 through each layer 304, 308, 312 of the suspended portion 252. The sensing layers 304, 308 define a thickness 316 that, in one embodiment, is from approximately one-half nanometer to approximately one hundred nanometers and preferably approximately one nanometer to approximately fifty nanometers. In one embodiment, the sensing layers 304, 308 are formed with ALD, and exemplary materials for forming the sensing layers include tin dioxide ($SnO_2$), tungsten trioxide ($WO_3$), zinc oxide (ZnO), and platinum. The active gas sensing area of the sensor device 100 is doubled compared to a sensor device including a sensing layer on only one side of a seed layer. In some embodiments, the suspended portion 252 includes (i) only the heater 312, (ii) only the heater 312 and the sensing layer 304, or (iii) only the heater 312 and the sensing layer 308. In an embodiment in which the suspended portion 252 includes only the heater 312, the heater 312 is configured as both the heater and the gas-sensitive layer.

The heater 312 is formed from a material that generates heat when exposed to an electrical current or other form of energy. The heater 312 is configured to heat the sensing layers 304, 308 to a desired sensing temperature. The heater 312 is also referred to herein as a heating layer, a heater layer, a resistive heater, a heater structure, and a heating structure. The heater 312 is formed from platinum, thermal silicon, doped silicon, composite materials, and the like. In one embodiment, the heater 312 is formed from a material(s) that is suitable for ALD.

The heater 312 is located between the two sensing layers 304, 308 and offers structural support to the sensing layers. Structuring the heater 312 with a sensing layer on the top and the bottom increases the energy efficiency of the sensor device 200 as compared to sensor devices having a sensing layer on only one side of the heater, since more of the heat energy developed by the heater is used to heat gas-sensitive material (i.e. the sensing layers 304, 308) rather than surrounding structures and air space.

In another embodiment, an additional structural layer (not shown) is formed between the sensing layer 304 and the heater 312 or between the sensing 308 and the heater to further strengthen the suspended portion 252. In yet another embodiment, a lower additional structural layer (not shown) is formed between the sensing layer 304 and the heater 312, and an upper additional structural layer is formed between the sensing 308 and the heater to further strengthen the suspended portion 252. The additional structural layer(s) is formed from aluminum oxide ($Al_2O_3$) or any other desired material and preferably a material that is suitable for ALD. Aluminum oxide functions well as an additional structural layer since it is an electrical insulator with a relatively high thermal conductivity.

Figure 5:
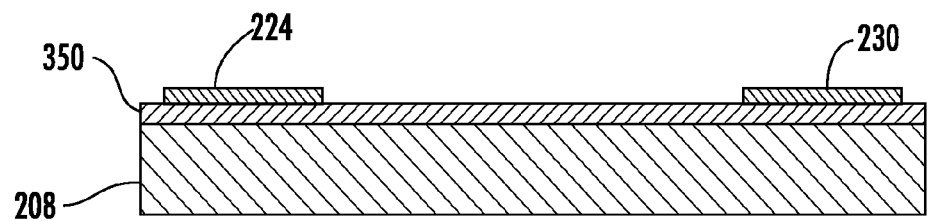
FIG. 5 is a side cross sectional view taken along a line similar to the line III-III of FIG. 4, showing a substrate, a partial insulator layer formed on the substrate, and two bond pads formed on the insulator layer.

As shown in FIG. 5, fabrication of the sensor device 200 of FIG. 3 begins with providing a substrate 208. The substrate 208 may be a portion of a larger substrate that is used to form a number of sensors and/or sensor devices 200. An initial insulator layer 350 is formed on the upper surface of the substrate 208. Next, the bond pads 224, 230 are formed on the initial insulator layer 350. The bond pads 224, 230 are formed from a conducting metal by any acceptable process such as one incorporating lithography and plasma etching.

Figure 6:
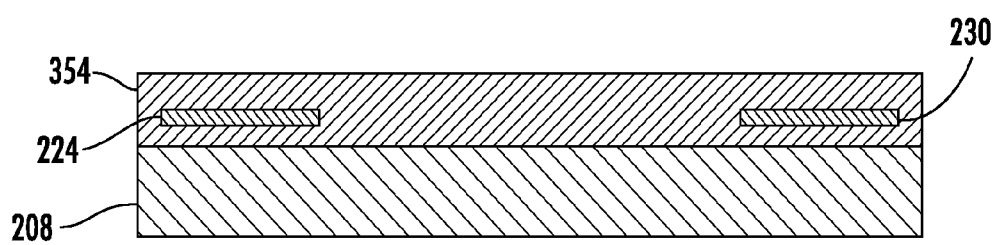
FIG. 6 is a side cross sectional view taken along a line similar to the line III-III of FIG. 4, of the device of FIG. 5 after the remainder of the insulator layer has been formed above the bond pads.

In FIG. 6, the remainder of the insulator layer 354 is then formed, thereby encapsulating the bond pads 224, 230. The insulator layer 354 is planarized if desired.

Figure 7:
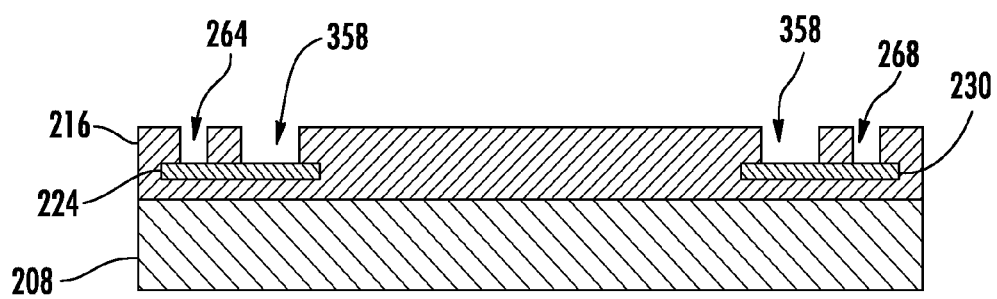
FIG. 7 is a side cross sectional view taken along a line similar to the line III-III of FIG. 4, of the device of FIG. 6 with openings formed through the insulator layer to expose the bond pads.

With reference to FIG. 7, portions of the bond pads 224, 230 are then exposed by trenching through the insulator layer 216 to form opening 264, 268, 358.

Figure 8:
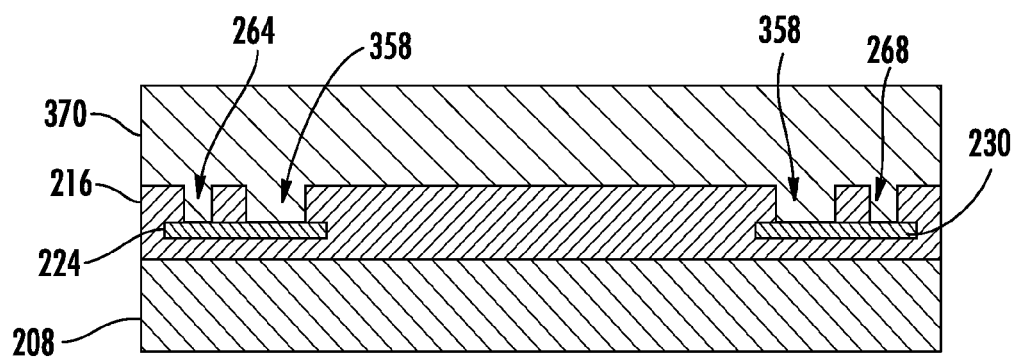
FIG. 8 is a side cross sectional view taken along a line similar to the line III-III of FIG. 4, of the device of FIG. 7 after a first portion of a sacrificial layer has been formed over the substrate.

As shown in FIG. 8, an initial sacrificial layer 370 (first portion) is then formed over the top of the insulator layer 216 and the openings 264, 268, 358.

Figure 9:
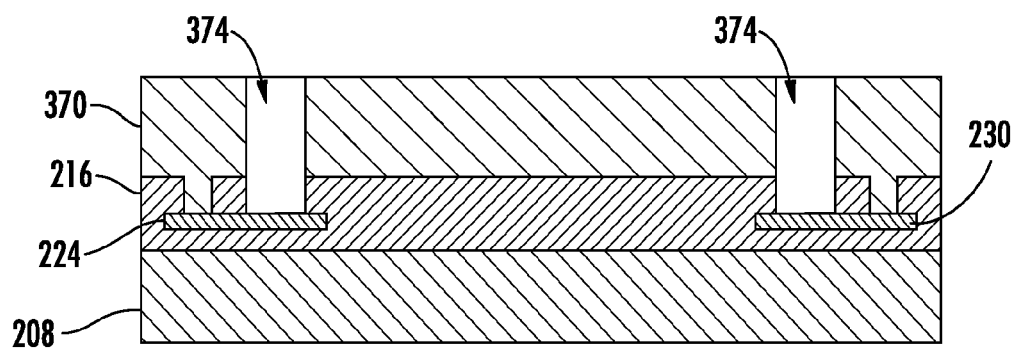
FIG. 9 is a side cross sectional view taken along a line similar to the line III-III of FIG. 4, of the device of FIG. 8 after openings through the first portion of the sacrificial layer to the bond pads have been formed.

With reference to FIG. 9, the initial sacrificial layer 370 is then etched to form trenches 374, which correspond to the desired size of the supports 238, 246 (FIG. 3).

Figure 10:
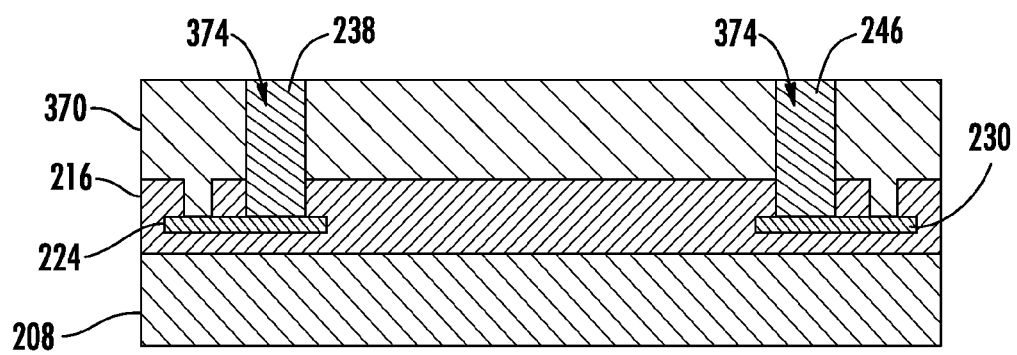
FIG. 10 is a side cross sectional view taken along a line similar to the line III-III of FIG. 4, of the device of FIG. 9 with supports formed within the openings in the first portion of the sacrificial layer.

In FIG. 10, the supports 238, 246 are formed by depositing material in the trenches 358, 374. Some material of the supports 238, 246 may be deposited on top of the initial insulator portion 370 and may be polished away if desired using a chemical mechanical polishing (CMP) process, for example. The material of the supports 238, 246 may be deposited using ALD or any other process/technique.

Figure 11:
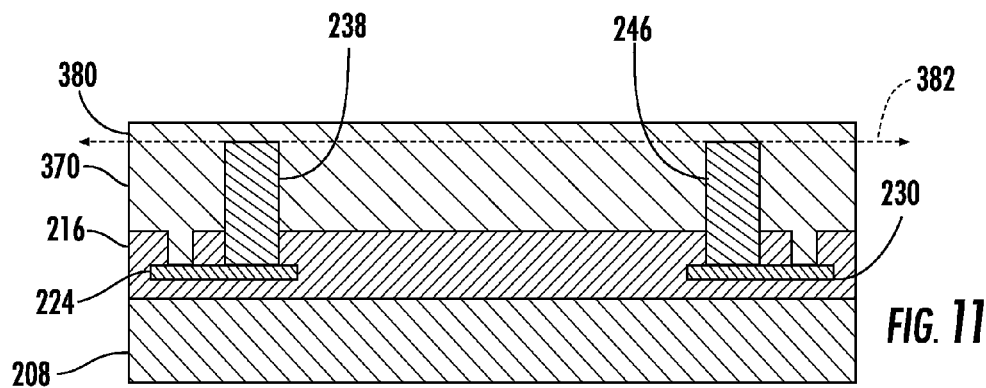
FIG. 11 is a side cross sectional view taken along a line similar to the line III-III of FIG. 4, of the device of FIG. 10 after a second portion of the sacrificial layer has been formed above the supports.

As shown in FIG. 11, a second portion 380 of the sacrificial layer is applied to the initial sacrificial layer 370. The second portion 380 is formed from the same material as the initial sacrificial layer 370 and is distinguished therefrom by the reference boundary line 382.

Figure 12:
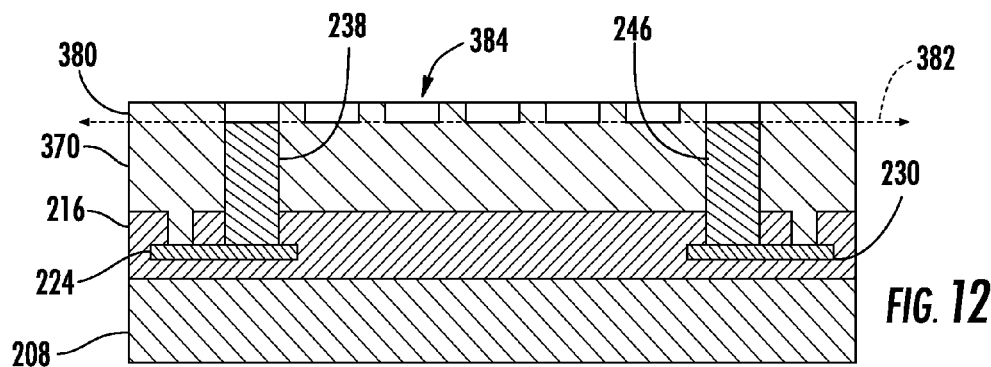
FIG. 12 is a side cross sectional view taken along the line XIII-XIII of FIG. 13, of the device of FIG. 11 after a serpentine trench has been formed in the second portion of the sacrificial layer.
Figure 13:
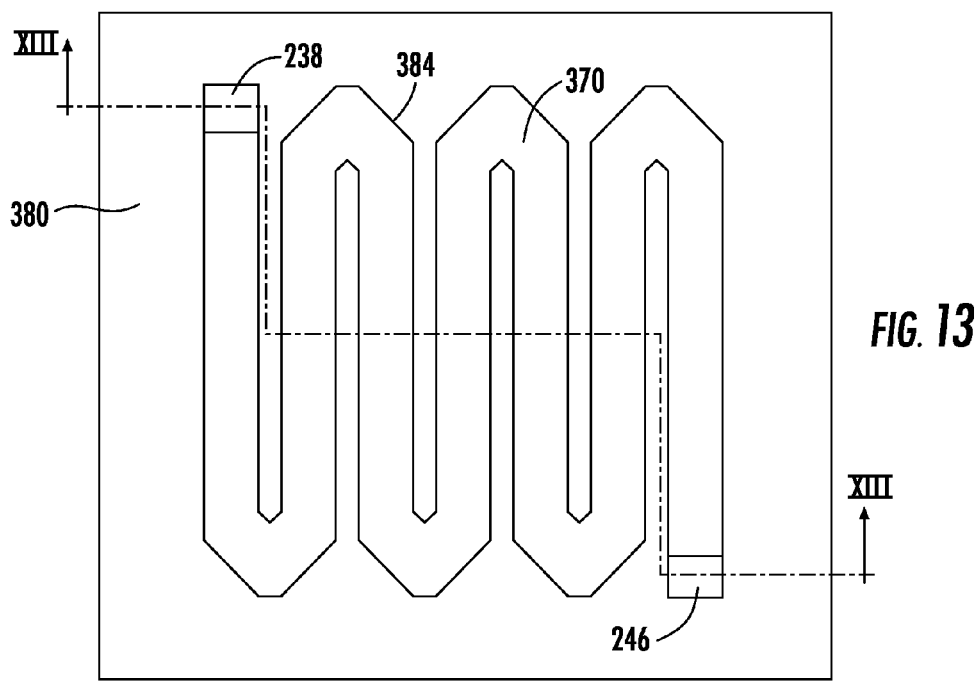
FIG. 13 is a top plan view of the device of FIG. 12 showing the serpentine trench and the upper surface of each of the supports.

Next, in FIGS. 12 and 13 the second portion 380 is trenched to define a serpentine-shaped trench 384 therein. The top surfaces of the supports 238, 246 are visible at the beginning and ending of the trench 384. The serpentine-shaped trench 384 extends through only the second portion 380 and, in one embodiment, is not formed in the initial sacrificial layer 370. The depth of the trench 384 is controlled by timing of the trenching process. In particular, the trenching process is carried out for a predetermined time period, with a longer duration of the predetermined time period corresponding to more trenching (deeper trench 384) and a shorter duration of the predetermined time period corresponding to less trenching (shallower trench 384). The depth of the trench 384 corresponds to the thickness 316 of the sensing layer 304.

Figure 14:
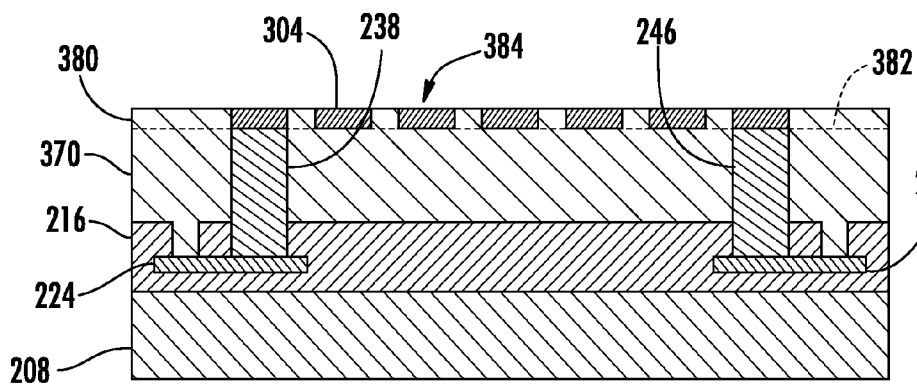
FIG. 14 is a side cross sectional view taken along a line similar to the line XIII-XIII of FIG. 13, of the device of FIG. 12 after the lower gas-sensitive portion has been formed in the serpentine trench.

FIG. 14 shows the sensing layer 304 deposited in the trench 384. The material of the sensing layer 304 is placed in contact with the supports 238, 246 so that the supports are electrically connected through the sensing layer. The second portion 380 of the sacrificial layer and the sensing layer 304 are planarized if desired.

As described above, in one embodiment, the sensor layer 304 (and the sensor layer 308) is formed using ALD. Atomic layer deposition is used to deposit materials by exposing a substrate to several different precursors sequentially. A typical deposition cycle begins by exposing a substrate to a precursor "A" which reacts with the substrate surface until saturation. This is referred to as a "self-terminating reaction." Next, the substrate is exposed to a precursor "B" which reacts with the surface until saturation. The second self-terminating reaction reactivates the surface. Reactivation allows the precursor "A" to react with the surface again. Typically, the precursors used in ALD include an organometallic precursor and an oxidizing agent such as water vapor or ozone.

The deposition cycle results, ideally, in one atomic layer being formed on the substrate. Thereafter, another layer may be formed by repeating the process. Accordingly, the final thickness of the layer is controlled by the number of cycles the substrate is exposed to. Moreover, deposition using an ALD process is substantially unaffected by the orientation of the particular surface upon which material is to be deposited. Accordingly, an extremely uniform thickness of material may be realized both on the upper and lower horizontal surfaces as well as on the vertical surfaces.

Figure 15:
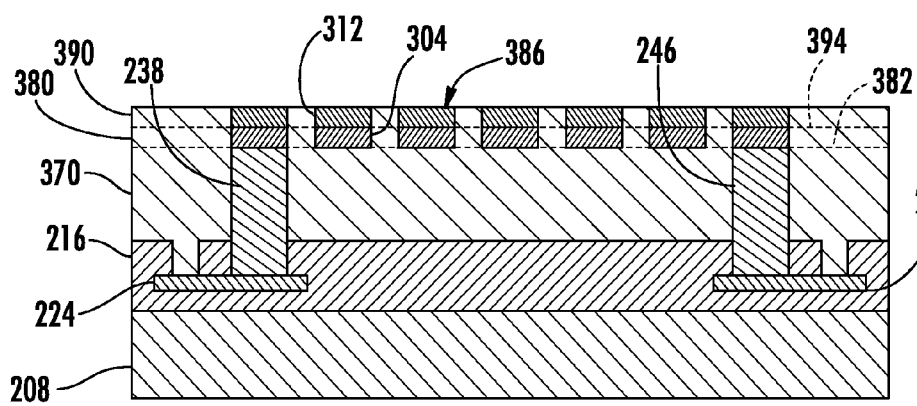
FIG. 15 is a side cross sectional view taken along a line similar to the line XIII-XIII of FIG. 13, of the device of FIG. 14 after a third portion of the sacrificial layer has been formed above the lower gas-sensitive portion, a serpentine trench has been formed in the third portion of the sacrificial layer, and the heater has been formed therein.

Next, FIG. 15 shows the heater 312 having been deposited in another serpentine shaped trench 286 using the same process as described above and shown in FIGS. 11-14. In particular, a third portion 390 of the sacrificial layer (distinguished by reference boundary line 394) is formed over the material of the sensing layer 304 and the second portion 380 of the sacrificial layer. Next, the serpentine trench 386 is etched in the third portion 390 of the sacrificial layer in a location that corresponds to the position of the serpentine trench 384. Thereafter, the material of the heater 312 is deposited in the trench 386 on top of the sensing layer 304. The third portion 390 of the sacrificial layer and the heater 312 are planarized if desired after deposition of the heater 312.

Figure 16:
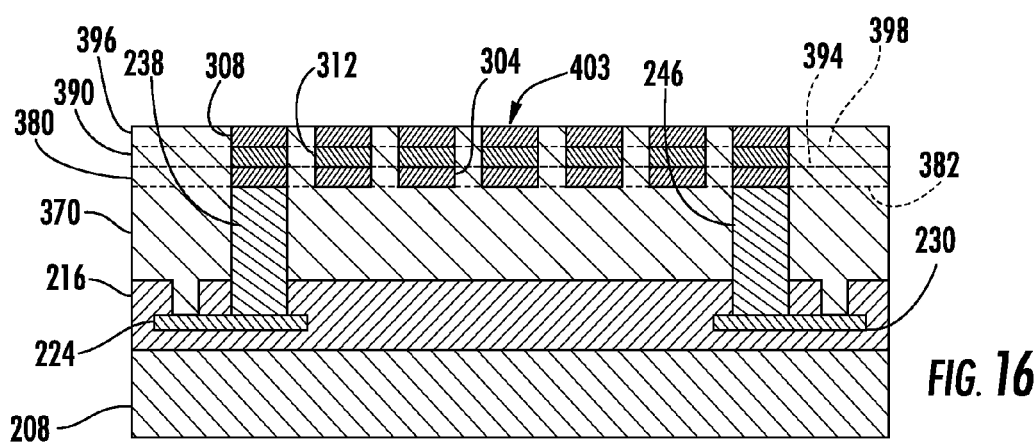
FIG. 16 is a side cross sectional view taken along a line similar to the line XIII-XIII of FIG. 13, of the device of FIG. 15 after a fourth portion of the sacrificial layer has been formed above the heater, a serpentine trench has been formed in the fourth portion of the sacrificial layer, and the upper gas-sensitive portion has been formed therein.

In FIG. 16, the process illustrated in FIGS. 11-14 is repeated yet again to form the sensing layer 308. In particular, a fourth portion 396 of the sacrificial layer (distinguished by reference boundary line 398) is formed over the material of the heater 312 and the third portion 390 of the sacrificial layer. Next, a serpentine trench 403 is etched in the fourth portion 396 of the sacrificial layer in a location that corresponds to the location of the serpentine trenches 384, 386. Thereafter, the material of the sensing layer 308 is deposited in the trench 403 on top of the heater 312. The fourth portion 396 of the sacrificial layer and the sensing layer 308 are planarized if desired after deposition of the sensing layer 308, and then the sacrificial layer 370, 380, 390, 396 is removed according to any desired process to suspend the suspended portion 252 above the insulator layer 216.

Figure 17:
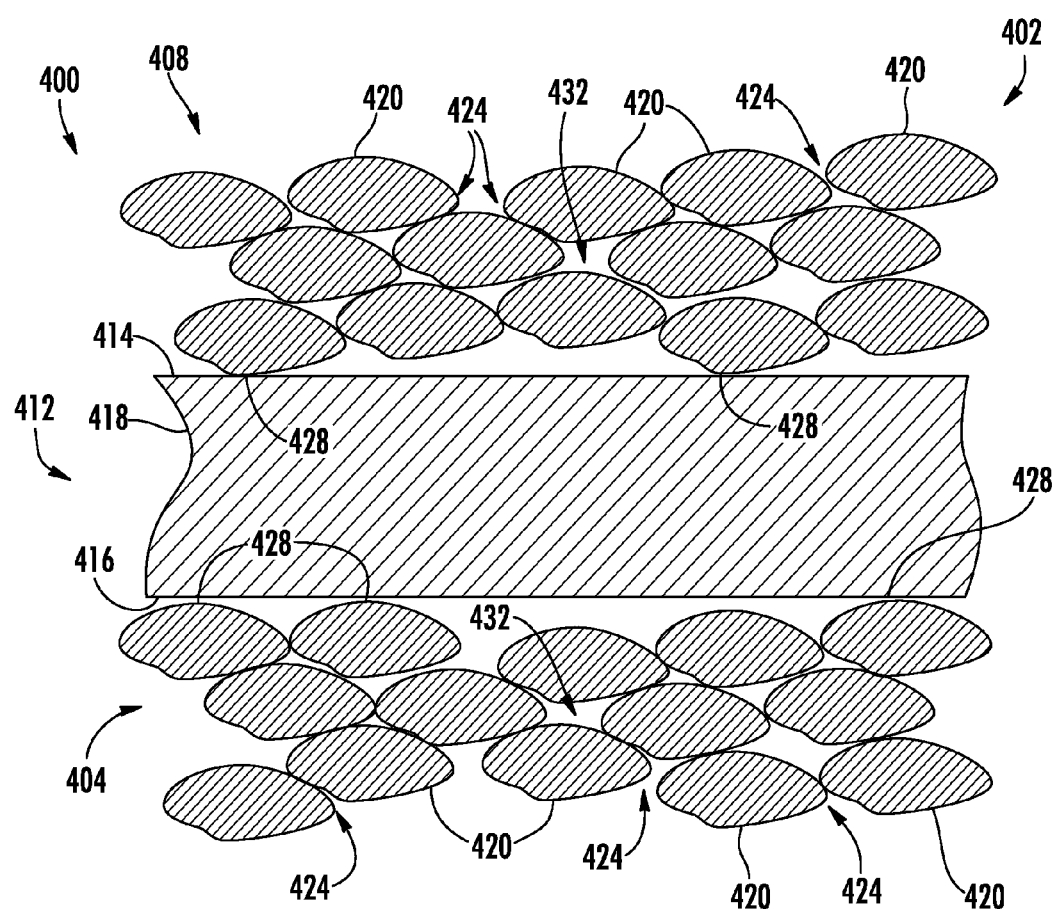
FIG. 17 is a cross sectional view of another embodiment of a thin-film gas sensor device including a non-suitable seed layer and a gas-sensitive portion formed on a bottom side and a top side of the seed layer, grain boundaries of the gas-sensitive portions are also shown.

As shown in FIG. 17, in another embodiment of a gas sensor device 400, a sensing layer 402 is formed on an upper surface 414, a lower surface 416, and side surfaces (not shown) of a suspended portion 418 of a seed layer 412 all during the same deposition step. In particular, to fabricate the gas sensor device 400, a conductive layer (not shown, see conductive layer 120) is formed over an insulator layer (not shown, see insulator layer 116) and a substrate (not shown, see substrate 108). Then a sacrificial layer (not shown, see sacrificial layer 154) is formed over the conductive layer. The sacrificial layer is patterned to define a trench including a suspended trench portion. Then the seed layer 412 is deposited within the trench of the sacrificial layer. Next, the seed layer 412 is patterned to finalize a shape of the suspended portion 418. After the seed layer 412 is patterned, the sacrificial layer is removed, which leaves the suspended portion 418 suspended over the conductive layer and exposes the lower surface 416 of the seed layer 412. With the upper surface 414, the lower surface 416, and the side surfaces of the suspended portion 418 exposed, ALD is used to deposit the sensing layer 402 on the surfaces of the seed layer 412 and in electrical communication with the conductive layer. Accordingly, the sensing layer 402 defines at least an upper sensing layer 404 and a lower sensing layer 408 each configured to detect a target gas.

As shown FIG. 17, the sensing layer 402 is a porous structure formed from a plurality of grains 420. The grains 420 are also referred to herein as crystallites. In general, each grain 420 contacts at least one other grain at a junction referred to as a grain boundary 424 (some of which are identified in FIG. 17). In an exemplary embodiment, the grains 420 have an average width of less than one nanometer, but may have any width as desired by those of ordinary skill in the art. The grains 420 are shaped/configured, in one embodiment, to form as many grain boundaries 424 as possible, so that the sensing layer 402 provides more grain boundaries 424 per unit length, as compared to prior art sensing layers. Accordingly, the grains 420 enable the sensing layer 402 to, in general, be thinner and smaller than prior art sensing layers, but have at least as many or more grain boundaries 424. Furthermore, in some embodiments, the sensing layer 402 may offer structural support to the suspended portion 418.

An exemplary method of forming the grains 420 of the sensing layer 402 includes depositing a material of the sensing layer(s) onto a "non-suitable" material of the seed layer 412. Typically, ALD is used to deposit a generally contiguous (non-porous) thin film of a material onto a seed layer formed from a "suitable material." The seed layer material is referred to as being "suitable" for the deposited material when, after a predetermined number of ALD cycles, the deposited material forms a polycrystalline thin film that is contiguous (i.e. non-porous) across at least a portion of the seed layer material. That is, the grains of deposited material formed by ALD on a "suitable" seed layer are formed tightly against each other so that there are substantially no air spaces therebetween. The materials therefore form a suitable pair of materials, since the resulting layer of deposited material is generally contiguous and non-porous. Accordingly, a gas-sensing layer formed from a material deposited on a "suitable" seed layer using ALD includes very few grain boundaries that are available to interact with a gas, because most of the grain boundaries are unexposed to the air space around the deposited material. It turns out, however, that the structure of the material deposited using ALD, is heavily dependent on the interaction of the deposited material with the material forming the seed layer.

In this exemplary embodiment, when forming the sensing layer 402, ALD is used to deposit the material of the sensing layer onto a "non-suitable" material of the seed layer 412. The seed layer 412 is referred to as being "non-suitable," since the deposited material forms a conforming polycrystalline layer (thin film) that is porous. The material of the sensing layer 402 and the non-suitable material of the seed layer 412 are referred to herein as a non-suitable pair of materials. Typically, the porous layer of deposited material is undesirable; however, when used as the sensing layer 402, the porous film of deposited material functions extraordinarily well. In particular, the non-suitable material of the seed layer 412 causes nucleation of the grains 420 of the deposited sensing material at the spaced-apart nucleation sites 428 (some of which are shown in FIG. 17). Accordingly, the grains 420 grow in far-isolated "islands" with numerous air spaces 432 (FIG. 17) therebetween. Additionally, the grains 420 contact each other at many grain boundaries 424, which promote adsorption (including chemisorption and heterogeneous catalysis) of the target gas. Even after several cycles of ALD the deposited material of the sensing layer 402 remains porous, and the grains 420 contact each other at many grain boundaries 424. The selection of the material of the sensing layer 402, the seed layer 412, and the number of cycles of ALD performed is based on at least the desired size of the grains 420, the density of the grains, the thickness of the sensing layer 402 portions, and the desired number of grain boundaries 424.

When used to form the sensing layer 402, the large number of grain boundaries 424 that are formed and the near instant heating of the sensing layer 402, encourages more rapid and more complete adsorption of the target gas on the sensing layers, as well as a more pronounced electrical change of the sensing layers in response to being exposed to the target gas. In short, the sensing layer 402 has enhanced gas sensing performance with a very fast response rate.

Figure 18:
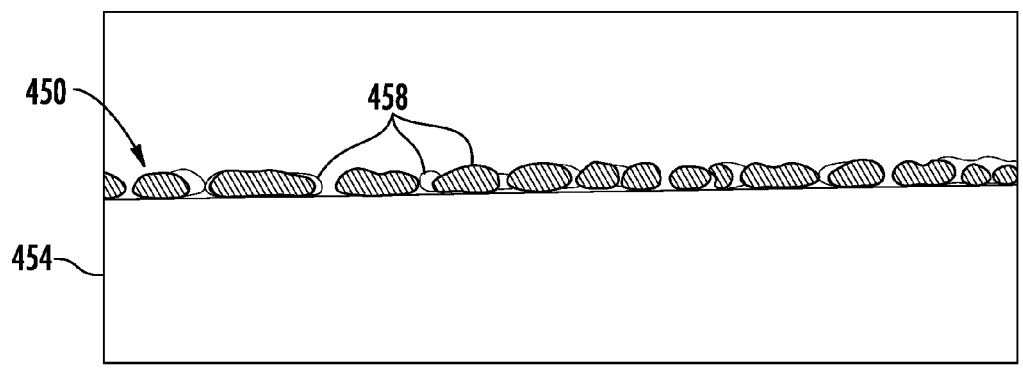
FIG. 18 is a transmission electron microscope view of a platinum layer formed using a process that is suitable for forming the gas-sensitive portions of the sensor device of at least FIGS. 2A and 17.
Figure 19:
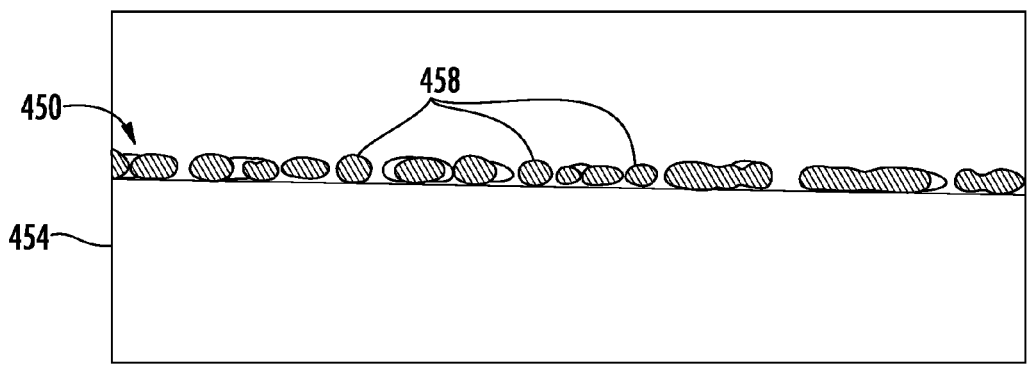
FIG. 19 is another transmission electron microscope view of a platinum layer formed using the process that is suitable for forming the gas-sensitive portions of the sensor device of at least FIGS. 2A and 17.

FIGS. 18 and 19 show two microscope views of an exemplary sensing layer 450 and a seed layer 454 that were formed from a non-suitable pair of materials. The seed layer 454 is formed from silicon dioxide and the deposited material of the sensing layer 450 is platinum. Accordingly, silicon dioxide and platinum form an exemplary pair of non-suitable materials. In FIG. 18, approximately one hundred fifty cycles of ALD were performed at approximately two hundred seventy degrees Celsius. In FIG. 19, approximately one hundred twenty five cycles of ALD were performed at approximately two hundred seventy degrees Celsius. The reduction in cycles results in smaller grains 458 and more space between each grain 458.

Figure 20:
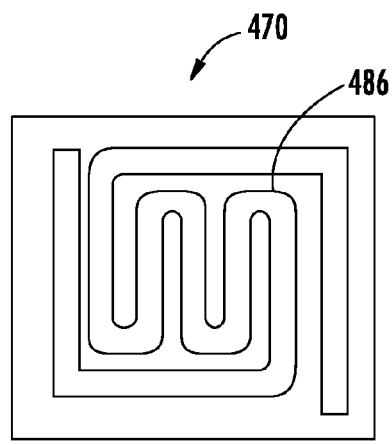
FIG. 20 is a top plan view of another embodiment of a gas sensor device having a serpentine shaped heater and gas-sensitive portions.
Figure 21:
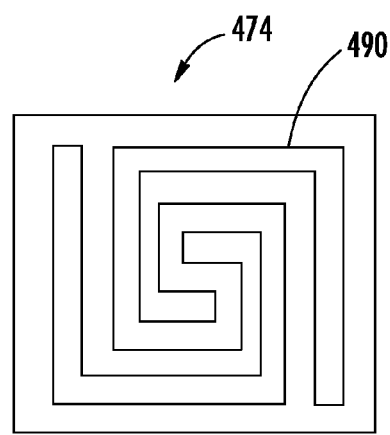
FIG. 21 is a top plan view of yet another embodiment of a gas sensor device having a serpentine shaped heater and gas-sensitive portions.
Figure 22:
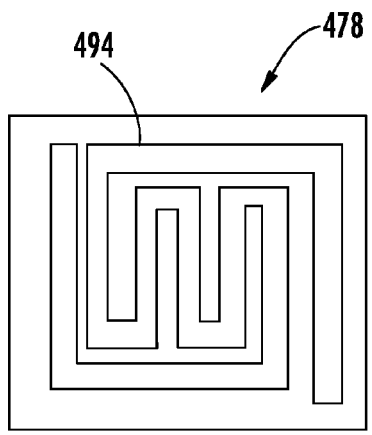
FIG. 22 is a top plan view of a further embodiment of a gas sensor device having a serpentine shaped heater and gas-sensitive portions.
Figure 23:
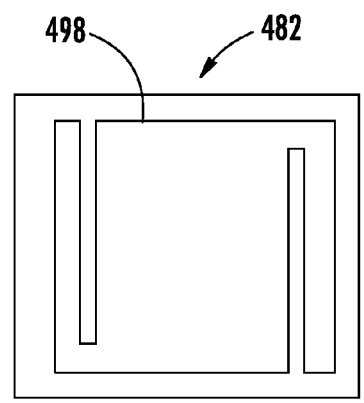
FIG. 23 is a top plan view of another embodiment of a gas sensor device having a rectangular-shaped heater and gas-sensitive portions.
Figure 24:
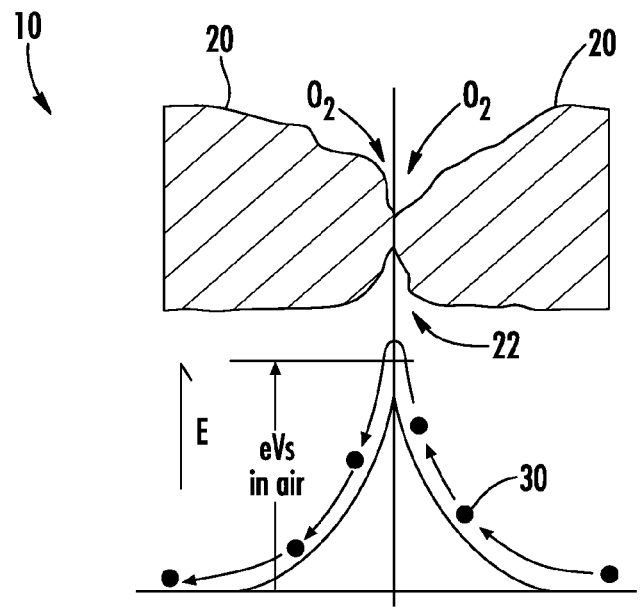
FIG. 24 is a cross sectional view of a grain boundary of a gas-sensitive layer of a prior art gas sensor in the presence of air, and a graph showing a corresponding potential barrier of the grain boundary.
Figure 25:
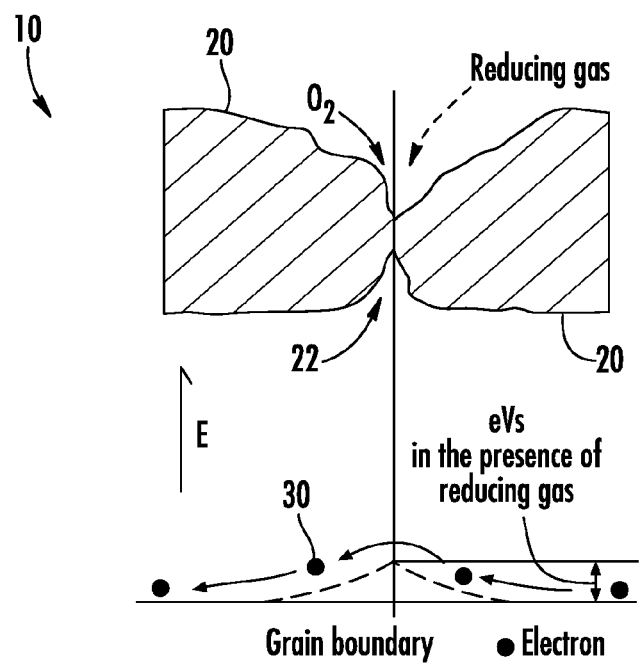
FIG. 25 is a cross sectional view of the grain boundary of FIG. 24 in the presence of air and a reducing gas, and a graph showing a corresponding potential barrier of the grain boundary.

As shown in FIGS. 20-23, four embodiments of the sensor device 470, 474, 478, 482 are shown. Each sensor device 470, 474, 478, 482 includes a suspended portion 486, 490, 494, 498. The sensor devices 470, 474, 478, 482 are identical to the sensor device 100 except that the shape of the suspended portions 486, 490, 494, 498 differ from the shape of the suspended portion 164. Specifically, the suspended portions 486, 490, 494 of FIGS. 20-22 illustrate a modified serpentine pattern. The suspended portion 498 of FIG. 23 is non-serpentine and defines a rectangular/square geometry.

In another embodiment of the sensor device 100, upon adsorption of the target gas by the sensing layer 128, the presence of the target gas is detected by the external circuit in response to at least one of the sensing layers undergoing a change in resonant frequency and/or a change in capacitance.

While the disclosure has been illustrated and described in detail in the drawings and foregoing description, the same should be considered as illustrative and not restrictive in character. It is understood that only the preferred embodiments have been presented and that all changes, modifications and further applications that come within the spirit of the disclosure are desired to be protected.

What is claimed is:

1. A semiconductor gas sensor device comprising:
a substrate;
a conductive layer supported by the substrate;
a non-suitable seed layer formed from a first material and including a first support portion supported by the conductive layer, a second support portion supported by the conductive layer, and a suspended seed portion extending from the first support portion to the second support portion and suspended above the conductive layer, and
a porous gas sensing layer portion formed from a second material and supported directly by the non-suitable seed layer and in electrical communication with the conductive layer, the first material and the second material forming a non-suitable pair of materials,
wherein the porous gas sensing layer portion is in direct contact with the conductive layer.

2. The semiconductor gas sensor device of claim 1, wherein:
the suspended seed portion defines a lower surface adjacent to the conductive layer and an opposite upper surface;
a first portion of the porous gas sensing layer portion is supported directly by the lower surface; and
a second portion of the porous gas sensing layer portion is supported directly by the upper surface.

3. The semiconductor gas sensor device of claim 1, wherein:
a first isolated portion of the conductive layer is electrically isolated from a second isolated portion of the conductive layer;
the first support portion extends from the first isolated portion; and
the second support portion extends from the second isolated portion.

4. The semiconductor gas sensor device of claim 1, wherein:
the porous gas sensing layer portion defines a suspended sensing portion that is supported directly by the suspended seed portion; and
the suspended sensing portion defines a substantially "U"-shaped cross-section in a plane perpendicular to the substrate.

5. The semiconductor gas sensor device of claim 1, wherein:
the porous gas sensing layer portion defines a suspended sensing portion that is supported directly by the suspended seed portion; and
the suspended sensing portion defines a substantially serpentine configuration.

6. The semiconductor gas sensor device of claim 1, wherein the porous gas sensing layer portion is configured to exhibit a change in at least one of a resistance, a capacitance, and a resonant frequency in the presence of a target gas.

7. The semiconductor gas sensor device of claim 1, wherein:
the first material is silicon dioxide, and
the second material is platinum.

8. A method of fabricating a semiconductor gas sensor device comprising:
forming a conductive layer above a substrate;
patterning the conductive layer to define a first isolated portion of the conductive layer that is electrically isolated from a second isolated portion of the conductive layer;
forming a sacrificial layer above the conductive layer;

patterning the sacrificial layer to define a first trench portion exposing an upper surface of the first isolated portion, a second trench portion exposing an upper surface of the second isolated portion, and a suspended trench portion that does not expose the conductive layer and that extends from the first trench portion to the second trench portion;

forming a non-suitable seed layer from a first material in the first trench portion, the second trench portion, and the suspended trench portion;

forming a porous gas sensing layer portion from a second material on the non-suitable seed layer and in electrical communication with the conductive layer, the second material deposited into the first trench portion, the second trench portion, and the suspended trench portion, and the first material and the second material forming a non-suitable pair of materials; and removing the sacrificial layer to suspend a suspended portion of the seed layer and the porous gas sensing layer portion above the conductive layer.

9. The method of claim 8, wherein forming the non-suitable seed layer comprises:

depositing the first material onto the sacrificial layer using atomic layer deposition, wherein the first material is aluminum oxide.

10. The method of claim 9, wherein forming the porous gas sensing layer portion comprises:

depositing the second material onto the non-suitable seed layer using atomic layer deposition, wherein the second material is platinum.

11. The method of claim 8, wherein patterning the sacrificial layer comprises:

trenching the suspended trench portion into a substantially serpentine configuration.

12. The method of claim 8, wherein patterning the sacrificial layer comprises:

trenching the suspended trench portion into a substantially rectangular configuration.

13. The method of claim 8, further comprising:

forming an insulator layer above the substrate; and forming the conductive layer above the insulating layer.

* * * * *